(12) United States Patent
O'Neil et al.

(10) Patent No.: US 8,807,136 B2
(45) Date of Patent: *Aug. 19, 2014

(54) SELF-SIZING ADJUSTABLE ENDOTRACHEAL TUBE

(75) Inventors: Michael P. O'Neil, Pleasanton, CA (US); Joel C. Colburn, Walnut Creek, CA (US)

(73) Assignee: Covidien LP, Mansfield, MA (US)

( * ) Notice: Subject to any disclaimer, the term of this patent is extended or adjusted under 35 U.S.C. 154(b) by 379 days.

This patent is subject to a terminal disclaimer.

(21) Appl. No.: 12/860,257

(22) Filed: Aug. 20, 2010

(65) Prior Publication Data

US 2010/0313896 A1 Dec. 16, 2010

Related U.S. Application Data (63) Continuation of application No. 11/541,381, filed on Sep. 29, 2006, now abandoned.

(51) Int. Cl.
*A61M 16/00* (2006.01)
*A62B 9/06* (2006.01)

(52) U.S. Cl.
USPC .................................................... 128/207.14

(58) Field of Classification Search
USPC ............. 128/207.14, 200.24, 207.15, 207.18; 606/198, 192; 604/96.01, 104–109, 20
See application file for complete search history.

(56) References Cited

U.S. PATENT DOCUMENTS

| | | | |
|---|---|---|---|
| 2,927,584 A | 3/1960 | Wallace | |
| 3,565,079 A * | 2/1971 | Jackson | 128/207.15 |
| 3,810,474 A | 5/1974 | Cross | |
| 3,822,238 A | 7/1974 | Blair et al. | |
| 3,975,350 A | 8/1976 | Hudgin et al. | |
| 4,018,231 A * | 4/1977 | Wallace | 128/207.15 |
| 4,340,046 A | 7/1982 | Cox | |
| 4,569,344 A | 2/1986 | Palmer | |
| 4,638,539 A | 1/1987 | Palmer | |
| 4,693,243 A * | 9/1987 | Buras | 128/207.15 |
| 4,696,296 A | 9/1987 | Palmer | |
| 4,722,335 A * | 2/1988 | Vilasi | 128/207.14 |

(Continued)

FOREIGN PATENT DOCUMENTS

| | | |
|---|---|---|
| CA | 2353007 | 6/2000 |
| DE | 19500550 | 7/1996 |

(Continued)

OTHER PUBLICATIONS

Ayşe Gönen Karakeçili et al.; "Comparison of Bacterial and Tissue Cell Initial Adhesion on Hydrophilic/Hydrophobic Biomaterials," J Biomater. Sci. Polymer Edn, vol. 13, No. 2, pp. 185-196 (2002).

(Continued)

*Primary Examiner* — Justine Yu
*Assistant Examiner* — Colin W Stuart
(74) *Attorney, Agent, or Firm* — Fletcher Yoder PC (57) ABSTRACT

There is disclosed an endotracheal tube which has a minimal cross-sectional profile for easy viewing of anatomical features during intubation. After the tube is placed into the trachea, the tube is adapted to increase the diameter. In this manner the tube diameter may be expanded to allow for decreased Work of Breathing (WOB) for patient, while not having so large a diameter as to cause tracheal discomfort.

7 Claims, 7 Drawing Sheets

(56) References Cited

U.S. PATENT DOCUMENTS

| | | | |
|---|---|---|---|
| 4,825,859 | A | 5/1989 | Lambert |
| 4,827,925 | A * | 5/1989 | Vilasi .................. 128/207.14 |
| 4,834,726 | A | 5/1989 | Lambert |
| 4,836,199 | A | 6/1989 | Palmer |
| 4,838,255 | A | 6/1989 | Lambert |
| 4,867,153 | A | 9/1989 | Lorenzen et al. |
| 4,872,579 | A | 10/1989 | Palmer |
| 4,927,412 | A | 5/1990 | Menasche |
| 4,938,741 | A | 7/1990 | Lambert |
| 4,963,313 | A | 10/1990 | Noddin et al. |
| 4,967,743 | A | 11/1990 | Lambert |
| 5,021,045 | A | 6/1991 | Buckberg et al. |
| 5,025,806 | A | 6/1991 | Palmer et al. |
| 5,029,580 | A | 7/1991 | Radford et al. |
| 5,038,777 | A * | 8/1991 | Dunn .................. 128/207.14 |
| 5,060,646 | A | 10/1991 | Page |
| 5,065,754 | A | 11/1991 | Jensen |
| 5,074,840 | A | 12/1991 | Yoon |
| 5,098,379 | A | 3/1992 | Conway et al. |
| 5,103,816 | A | 4/1992 | Kirschbaum et al. |
| 5,107,829 | A | 4/1992 | Lambert |
| 5,120,322 | A | 6/1992 | Davis et al. |
| 5,122,122 | A | 6/1992 | Allgood |
| 5,133,345 | A | 7/1992 | Lambert |
| 5,135,516 | A | 8/1992 | Sahatjian et al. |
| 5,137,671 | A | 8/1992 | Conway et al. |
| 5,158,569 | A | 10/1992 | Strickland et al. |
| 5,165,420 | A | 11/1992 | Strickland |
| 5,190,810 | A | 3/1993 | Kirschbaum et al. |
| 5,199,427 | A | 4/1993 | Strickland |
| 5,207,643 | A | 5/1993 | Davis |
| 5,215,522 | A | 6/1993 | Page et al. |
| 5,392,774 | A * | 2/1995 | Sato .................. 128/207.15 |
| 5,407,423 | A | 4/1995 | Yoon |
| 5,417,671 | A | 5/1995 | Jackson |
| 5,423,745 | A | 6/1995 | Todd et al. |
| 5,439,457 | A | 8/1995 | Yoon |
| 5,447,505 | A | 9/1995 | Valentine et al. |
| 5,451,204 | A | 9/1995 | Yoon |
| 5,452,715 | A * | 9/1995 | Boussignac .............. 128/207.15 |
| 5,466,231 | A | 11/1995 | Cercone et al. |
| 5,469,864 | A | 11/1995 | Rosenblatt |
| 5,482,740 | A | 1/1996 | Conway et al. |
| 5,484,426 | A | 1/1996 | Yoon |
| 5,487,730 | A | 1/1996 | Maracadis et al. |
| 5,490,839 | A | 2/1996 | Wang et al. |
| 5,494,029 | A | 2/1996 | Lane et al. |
| 5,496,276 | A | 3/1996 | Wang et al. |
| 5,501,669 | A | 3/1996 | Conway et al. |
| 5,507,284 | A | 4/1996 | Daneshvar |
| 5,509,899 | A | 4/1996 | Fan et al. |
| 5,524,642 | A | 6/1996 | Rosenblatt |
| 5,545,132 | A | 8/1996 | Fagan et al. |
| 5,556,391 | A | 9/1996 | Cercone et al. |
| 5,593,718 | A | 1/1997 | Conway et al. |
| 5,599,292 | A | 2/1997 | Yoon |
| 5,599,299 | A | 2/1997 | Weaver et al. |
| 5,599,321 | A | 2/1997 | Conway et al. |
| 5,611,336 | A | 3/1997 | Page et al. |
| 5,613,950 | A | 3/1997 | Yoon |
| 5,647,358 | A * | 7/1997 | Vilasi .................. 128/207.14 |
| 5,649,902 | A | 7/1997 | Yoon |
| 5,670,111 | A | 9/1997 | Conway et al. |
| 5,674,192 | A | 10/1997 | Sahatjian et al. |
| 5,693,014 | A | 12/1997 | Abele et al. |
| 5,694,922 | A | 12/1997 | Palmer |
| 5,700,239 | A | 12/1997 | Yoon |
| 5,714,110 | A | 2/1998 | Wang et al. |
| 5,715,815 | A | 2/1998 | Lorenzen et al. |
| 5,720,726 | A | 2/1998 | Marcadis et al. |
| 5,722,931 | A | 3/1998 | Heaven |
| 5,730,123 | A | 3/1998 | Lorenzen |
| 5,733,252 | A | 3/1998 | Yoon |
| 5,735,271 | A | 4/1998 | Lorenzen et al. |
| 5,738,901 | A | 4/1998 | Wang et al. |
| 5,765,559 | A | 6/1998 | Kim |
| 5,769,882 | A | 6/1998 | Fogarty et al. |
| 5,810,786 | A | 9/1998 | Jackson et al. |
| 5,827,215 | A | 10/1998 | Yoon |
| 5,843,017 | A | 12/1998 | Yoon |
| 5,843,028 | A | 12/1998 | Weaver et al. |
| 5,843,060 | A | 12/1998 | Cercone |
| 5,843,089 | A | 12/1998 | Sahatjian et al. |
| 5,855,563 | A * | 1/1999 | Kaplan et al. .................. 604/509 |
| 5,868,719 | A | 2/1999 | Tsukernik |
| 5,937,861 | A * | 8/1999 | Augustine ................ 128/207.15 |
| 5,951,597 | A | 9/1999 | Westlund et al. |
| 5,954,706 | A | 9/1999 | Sahatjian |
| 5,954,740 | A | 9/1999 | Ravenscroft et al. |
| 5,971,954 | A | 10/1999 | Conway et al. |
| 5,997,503 | A | 12/1999 | Willis et al. |
| 5,997,546 | A | 12/1999 | Foster et al. |
| 6,010,480 | A | 1/2000 | Abele et al. |
| 6,012,451 | A | 1/2000 | Palmer |
| 6,048,332 | A | 4/2000 | Duffy et al. |
| 6,110,192 | A | 8/2000 | Ravenscroft et al. |
| 6,129,547 | A | 10/2000 | Cise |
| 6,169,123 | B1 | 1/2001 | Cercone |
| 6,210,364 | B1 | 4/2001 | Anderson |
| 6,213,975 | B1 | 4/2001 | Laksin |
| 6,214,895 | B1 | 4/2001 | Cercone |
| 6,227,200 | B1 | 5/2001 | Crump et al. |
| 6,240,321 | B1 | 5/2001 | Janke et al. |
| 6,248,088 | B1 | 6/2001 | Yoon |
| 6,264,631 | B1 | 7/2001 | Willis et al. |
| 6,264,633 | B1 | 7/2001 | Knorig |
| 6,277,089 | B1 | 8/2001 | Yoon |
| 6,312,421 | B1 | 11/2001 | Boock |
| 6,322,586 | B1 | 11/2001 | Monroe et al. |
| 6,328,710 | B1 | 12/2001 | Wang et al. |
| 6,358,266 | B1 * | 3/2002 | Bonutti .................. 606/190 |
| 6,364,856 | B1 | 4/2002 | Ding et al. |
| 6,394,093 | B1 | 5/2002 | Lethi |
| 6,395,012 | B1 | 5/2002 | Yoon et al. |
| 6,398,266 | B1 | 6/2002 | Crump |
| 6,409,716 | B1 | 6/2002 | Sahatjian et al. |
| 6,494,203 | B1 | 12/2002 | Palmer |
| 6,524,272 | B1 | 2/2003 | Berry, Sr. |
| 6,526,977 | B1 | 3/2003 | Göbel |
| 6,543,451 | B1 | 4/2003 | Crump et al. |
| 6,551,272 | B2 | 4/2003 | Göbel |
| 6,572,813 | B1 | 6/2003 | Zhang et al. |
| 6,584,970 | B1 | 7/2003 | Crump et al. |
| 6,588,425 | B2 | 7/2003 | Rouns et al. |
| 6,588,427 | B1 | 7/2003 | Carlsen et al. |
| 6,602,218 | B2 | 8/2003 | Yoon |
| 6,602,219 | B2 | 8/2003 | Madsen et al. |
| 6,609,520 | B1 | 8/2003 | Carlsen et al. |
| 6,612,304 | B1 | 9/2003 | Cise et al. |
| 6,613,025 | B1 | 9/2003 | Palasis |
| 6,615,835 | B1 | 9/2003 | Cise et al. |
| 6,620,128 | B1 | 9/2003 | Simhambhatla |
| 6,623,450 | B1 | 9/2003 | Dutta |
| 6,629,530 | B2 | 10/2003 | Cise |
| 6,632,091 | B1 | 10/2003 | Cise et al. |
| 6,651,664 | B1 | 11/2003 | Lomholt |
| 6,688,306 | B1 | 2/2004 | Cise et al. |
| 6,698,424 | B2 | 3/2004 | Madsen et al. |
| 6,726,696 | B1 | 4/2004 | Houser et al. |
| 6,745,773 | B1 | 6/2004 | Gobel |
| 6,767,340 | B2 | 7/2004 | Willis et al. |
| 6,769,430 | B1 | 8/2004 | Carlsen et al. |
| 6,770,066 | B1 | 8/2004 | Weaver et al. |
| 6,786,876 | B2 | 9/2004 | Cox |
| 6,790,221 | B2 | 9/2004 | Monroe et al. |
| 6,802,317 | B2 | 10/2004 | Göbel |
| 6,805,125 | B1 | 10/2004 | Crump et al. |
| 6,808,521 | B1 | 10/2004 | McMichael |
| 6,908,449 | B2 | 6/2005 | Willis et al. |
| 6,916,307 | B2 | 7/2005 | Willis et al. |
| 6,923,786 | B2 | 8/2005 | Rouns et al. |
| 6,979,420 | B2 | 12/2005 | Weber |
| 7,040,321 | B2 | 5/2006 | Göbel |
| 7,056,466 | B2 | 6/2006 | Wang et al. |

(56) References Cited

U.S. PATENT DOCUMENTS

| | | |
|---|---|---|
| 2001/0041861 A1 | 11/2001 | Gobel |
| 2002/0077603 A1 | 6/2002 | Willis et al. |
| 2002/0077604 A1 | 6/2002 | Willis et al. |
| 2002/0078960 A1 | 6/2002 | Cise |
| 2002/0078963 A1 | 6/2002 | Rouns et al. |
| 2002/0082552 A1 | 6/2002 | Ding et al. |
| 2002/0091375 A1 | 7/2002 | Sahatjian et al. |
| 2002/0110657 A1 | 8/2002 | Wang et al. |
| 2002/0193753 A1 | 12/2002 | Rouns et al. |
| 2003/0000526 A1 | 1/2003 | Gobel |
| 2003/0032407 A1 | 2/2003 | Mages |
| 2003/0066532 A1 | 4/2003 | Gobel |
| 2003/0069620 A1 | 4/2003 | Li |
| 2003/0111077 A1 | 6/2003 | Hooser et al. |
| 2003/0116162 A1 | 6/2003 | Madsen et al. |
| 2003/0116963 A1 | 6/2003 | Teuscher et al. |
| 2003/0225369 A1 | 12/2003 | McMichael et al. |
| 2003/0225392 A1 | 12/2003 | McMichael et al. |
| 2003/0225393 A1 | 12/2003 | McMichael et al. |
| 2004/0024363 A1 | 2/2004 | Goldberg |
| 2004/0079376 A1 | 4/2004 | Melker |
| 2004/0092870 A1 | 5/2004 | Squire et al. |
| 2004/0106899 A1 | 6/2004 | McMichael et al. |
| 2004/0106900 A1 | 6/2004 | Triebes et al. |
| 2004/0106901 A1 | 6/2004 | Letson et al. |
| 2004/0193100 A1 | 9/2004 | Van Hooser et al. |
| 2004/0193101 A1 | 9/2004 | Van Hooser et al. |
| 2004/0215142 A1 | 10/2004 | Matheis et al. |
| 2004/0255952 A1 | 12/2004 | Carlsen et al. |
| 2005/0004560 A1 | 1/2005 | Cox |
| 2005/0033267 A1 | 2/2005 | Decaria |
| 2005/0033268 A1 | 2/2005 | Decaria |
| 2005/0033269 A1 | 2/2005 | Decaria |
| 2005/0038381 A1 | 2/2005 | McMichael |
| 2005/0065468 A1 | 3/2005 | Goebel |
| 2005/0124932 A1 | 6/2005 | Foster et al. |
| 2005/0124935 A1 | 6/2005 | McMichael |
| 2007/0095351 A1 | 5/2007 | Gobel |
| 2008/0064839 A1 | 3/2008 | Hadba et al. |
| 2010/0313895 A1* | 12/2010 | O'Neil et al. ............ 128/207.15 |

FOREIGN PATENT DOCUMENTS

| | | |
|---|---|---|
| EP | 0596517 | 5/1994 |
| EP | 0884061 | 12/1998 |
| EP | 1005877 | 6/2000 |
| EP | 1267981 | 1/2003 |
| GB | 2168256 | 11/1985 |
| WO | WO2005018713 | 3/2005 |

OTHER PUBLICATIONS

Blunt et al.; "Gel Lubrication of the Tracheal Tube Cuff Reduces Pulmonary Aspiration," 2001 American Society of Anesthesiologists, Inc. Lippincott Williams & Wilkins, Inc.; Anesthesiology, V. 95, No. 2, Aug. 2001.

Dullenkopf, et al., "Fluid leakage past tracheal tube cuffs: evaluation on the new Microcuff endotracheal tube," Intensive Care Medicine, (2003) vol. 29, pp. 1849-1853.

Sartomer Application Bulletin; "Functional Acrylic Monomers as Modifiers for PVC Plastisol Formulations," pp. 1-6.

Shintani; "Modification of Medical Device Surface to Attain Anti-Infection," National Institute of Health Sciences; Trends Biomater. Artif. Organs, vol. 18(1), pp. 1-8 (2004).

Tecogel brochure page, Noveon Thermedics Polymer Products, Oct. 2003.

www.clinicaltrials.gov/ct2/show/NCT00221377 Sep. 13, 2005, 7 pgs.

* cited by examiner

SELF-SIZING ADJUSTABLE ENDOTRACHEAL TUBE

CROSS-REFERENCE TO RELATED APPLICATION

This application is a continuation of patent application Ser. No. 11/541,381, entitled "Self-Sizing Adjustable Endotracheal Tube", filed Sep. 29, 2006, which is herein incorporated by reference in its entirety.

BACKGROUND OF THE INVENTION

1. Field of the Invention

The present invention relates to medical devices, and more particularly, to airway devices, such as tracheal tubes.

2. Description of the Related Art

This section is intended to introduce the reader to various aspects of art that may be related to the present invention which is described and/or claimed below. This discussion is believed to be helpful in providing the reader with background information to facilitate a better understanding of the various aspects of the present invention. Accordingly, it should be understood that these statements are to be read in this light, and not as admissions of prior art.

In the course of treating a patient, a tube or other medical device may be used to control the flow of air, food, fluids, or other substances into and/or out of the patient. For example, medical devices, such as tracheal tubes, may be used to control the flow of one or more substances into or out of a patient. In many instances, it is desirable to provide a seal between the outside of the tube or device and the interior of the passage in which the tube or device is inserted. In this way, substances can only flow through the passage via the tube or other medical device, allowing a medical practitioner to maintain control over the type and amount of substances flowing into and out of the patient.

Tracheal tubes may be used to control the flow of air or other gases through a patient's trachea. Such tracheal tubes may include endotracheal tubes and tracheostomy tubes. To seal these types of tracheal tubes, inflatable cuffs are sometimes associated with these tubes. When inflated, these cuffs generally expand into the surrounding trachea to seal the tracheal passage around the circumference of the tube. A high-quality seal against the tracheal passageway allows a ventilator to perform efficiently.

Generally, endotracheal tubes are available in a subset of sizes from which doctors may select the closest approximate size for a particular patient. The difference in tube sizes may generally reflect both differences in the length of the tube as well as different tube diameters. In particular, doctors may wish to select an endotracheal tube with an appropriate diameter in order to allow the tube to be easily inserted into the patient while providing the largest possible airway path for respiratory gases. For example, an endotracheal tube with too small a tube diameter may be associated with an increased work of breathing for the patient. Conversely, an endotracheal tube with too large a tube diameter presents certain disadvantages. For example, if the outer diameter of the endotracheal tube is too large, it can become difficult to navigate through the larynx and trachea. Thus, too large an endotracheal tube may increase the time it takes to intubate the patient. Also, a large endotracheal tube can prove somewhat uncomfortable for the patient. For instance, irritation of the tracheal walls can result from increased contact with the endotracheal tube.

SUMMARY

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

There is provided a tracheal tube that includes a distal end portion; an intermediate portion connected to the distal end portion; and a proximal end portion connected to the intermediate portion, wherein the intermediate portion is adapted to change its diameter.

There is also provided a method for sealing a patient's trachea that includes inserting an tracheal tube into a patient's trachea; and expanding a portion of the tracheal tube to conform to the contours of the tracheal walls.

There is also provided a method of manufacturing a tracheal tube that includes providing a distal end portion; providing an intermediate portion connected to the distal end portion; and providing a proximal end portion connected to the intermediate portion; wherein the intermediate portion is adapted to change its diameter.

There is also provided a tracheal tube that includes: a distal end portion; an intermediate portion comprising an inner layer and an outer layer connected to the distal end portion; and a proximal end portion connected to the intermediate portion, wherein the intermediate portion adapted to change its diameter by expanding a gap between the inner layer and the outer layer.

There is also provided a method for sealing a patient's trachea that includes: inserting a tracheal tube into a patient's trachea, wherein the tracheal tube comprises an inner layer and an outer layer along at least a portion of the tube; and expanding a gap between the inner layer and the outer layer of the tracheal tube so that the outer layer of the tube substantially conforms to the tracheal walls.

There is also provided a method of manufacturing a tracheal tube that includes: providing a distal end portion of a tube; providing an intermediate portion comprising an inner layer and an outer layer connected to the distal end portion; and providing a proximal end portion connected to the intermediate portion, wherein the intermediate portion adapted to change its diameter by expanding a gap between the inner layer and the outer layer.

There is also provided a method for sealing a patient's trachea that includes: inserting a tracheal tube into a patient's trachea; expanding a portion of the tracheal tube to substantially conform to the contours of the tracheal walls during a period of patient expiration; and contracting a portion of the tracheal tube so that the tracheal tube has an outer diameter that is less than the diameter of the tracheal walls during a period of patient inspiration.

There is also provided a system that includes: a tracheal tube comprising a lumen adapted to pneumatically expand or contract a diameter of at least a portion of the tracheal tube; and a medical monitor adapted to be operatively coupled to a tracheal tube, the medical monitor comprising instructions for: increasing pressure to the lumen to expand a portion of the tracheal tube to substantially conform to the contours of the tracheal walls during a period of patient expiration; and decreasing pressure to the lumen to contract a portion of the tracheal tube so that at least a portion of the tracheal tube has an outer diameter that is less than the diameter of the tracheal walls during a period of patient inspiration.

There is also provided a computer readable medium that includes: code for increasing pressure to the lumen of an expandable-diameter tracheal tube to expand a portion of a tracheal tube to substantially conform to the contours of the tracheal walls during a period of patient expiration; and code for decreasing pressure to the lumen of an expandable-diameter tracheal tube to contract a portion of the tracheal tube so that at least a portion of the tracheal tube has an outer diameter that is less than the diameter of the tracheal walls during a period of patient inspiration.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Provided herein are adjustable-diameter medical devices that may assume a relatively small outer diameter for easy viewing of anatomical features during insertion, making insertion of these devices easier for the clinician. Further, such devices may decrease patient discomfort during insertion as their relatively smaller cross-sectional profiles, as compared to a typical endotracheal tube, may not irritate the patient's internal passageways. For example, once the endotracheal tube has been inserted into the trachea, both the inner diameter and the outer diameter of the endotracheal tube may be increased in order to seal the tube against the trachea and to increase the total volume of air that may pass through the tube. An endotracheal tube having a large enough inner diameter may allow a patient to expend less energy during exhalation, as respiratory gases may flow more easily in and out of a larger diameter tube. In certain embodiments, the tube outer diameter may be increased to equal the diameter of the trachea. In such an embodiment, the endotracheal tube may provide an enhanced seal against the tracheal walls. As the endotracheal tube outer walls may contact the trachea over its length, the length of the seal may be increased relative to a standard cuffed tube, and a longer seal may be associated with improved sealing.

The adjustable-diameter tubes as provided herein may be used in conjunction with any suitable medical device. In certain embodiments, the tubes as provided herein may be used in conjunction with a catheter, a stent, a rib or batten, a feeding tube, an intravenous tube, an endotracheal tube, a tracheostomy tube, a circuit, an airway accessory, a connector, an adapter, a filter, a humidifier, a nebulizer, or a prosthetic, in various embodiments.

Figure 1:
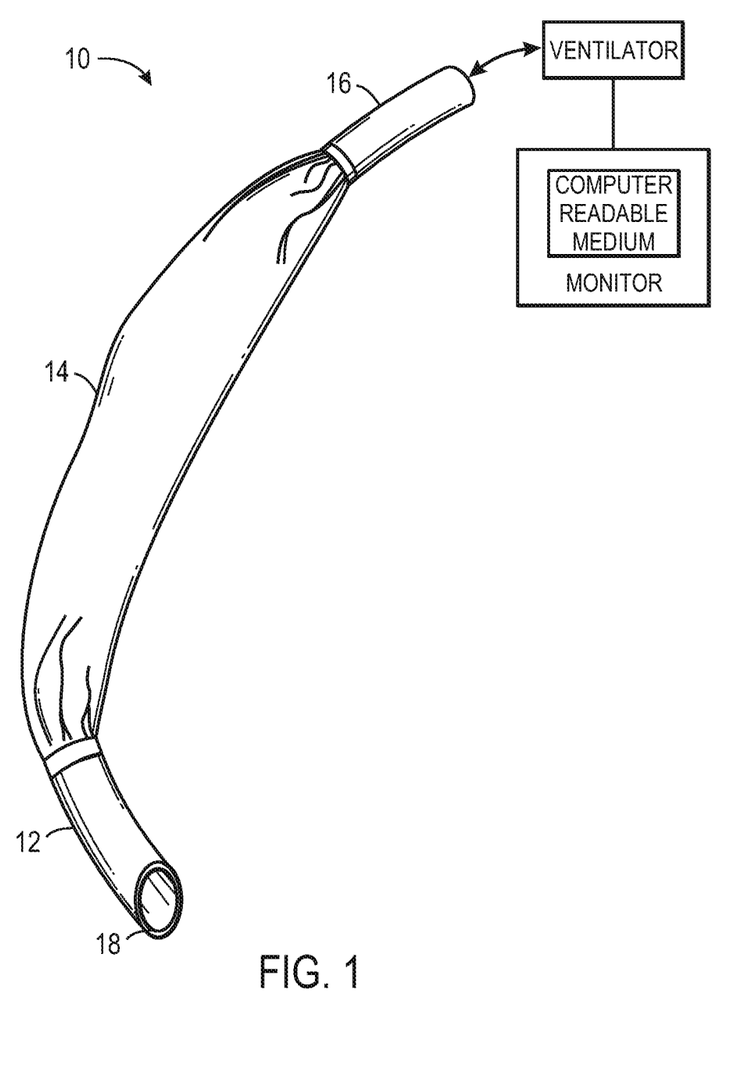
FIG. 1 illustrates an endotracheal tube with an expandable intermediate portion in accordance with aspects of the present invention.

An example of such a device is an endotracheal tube 10, as depicted in FIG. 1. The endotracheal tube 10 includes a distal end portion 12 for intubation into a patient, an intermediate portion 14, and a proximal end portion 16 for connection to other medical systems, such as a ventilator (not shown). The distal end portion 12 may be shaped and sized as in typical endotracheal tubes. Whereas the intermediate portion 14 may be made of a structure capable of expanding, discussed in more detail below, the distal end portion 12 may be made of any suitable material that is suitably rigid. For example, the distal end portion 12 may be polyvinyl chloride with a hardness of 84-90 Shore A. The relative rigidity of the distal end portion 12 facilitates guiding the endotracheal tube 10 through the patient's larynx and trachea. As such, the distal end portion 12 may generally be more rigid than the intermediate portion 14 to facilitate guidance through these narrow passageways. Suitable materials for the distal end portion 12 may also include silicone, rubber, or polyurethane. Generally, the distal end portion 12 may be attached to the intermediate portion 14 by any suitable means, such as by adhesives or heat sealing, solvent bonding, RF sealing, ultrasonic welding. Alternatively, the endotracheal tube 10 may be extruded as a single tube and the intermediate portion may be blow-molded to have relatively thinner walls than the distal end portion 12 or the proximal end portion 16. In a specific embodiment, the outer diameter of the distal end portion 12 may be approximately 1-14 millimeters, which may vary depending on whether the patient is a pediatric patient or an adult patient. The distal end portion 12 may be any suitable length. For example, in certain embodiments, the distal end portion 12 may be 10-50 millimeters. In addition, the distal end portion 12 of the endotracheal tube 10 may include an opening 17 (see FIG. 2) in the side wall of the distal end portion 12 near the distal opening 18. This opening 17 is often called a "Murphy eye" and may serve as an alternate flow path in the event that the distal opening 18 becomes blocked. Also, the distal opening 18 may be beveled to allow for smoother insertion through the larynx and trachea.

As with the distal end portion 12, the proximal end portion 16 may be formed from conventional plastics or polymers, including medical grade polyvinyl chloride. Generally, the proximal end portion 16 may be attached to the intermediate portion 14 by any suitable means, such as by adhesives or heat sealing. The proximal end portion 16 may be capable of being attached and detached from other medical systems, including a ventilator. As such, the proximal end portion 16 may terminate with a coupling, such as a quick-disconnect coupling (not shown) or a standard 15 mm outer diameter coupling. In a specific embodiment, the outer diameter of the proximal end portion 16 may be approximately 2-11 millimeters, which may vary depending on whether the patient is a pediatric patient or an adult patient. The proximal end portion 16 may be any suitable length. For example, in certain embodiments, the proximal end portion 16 may be 0.1-50 or more centimeters. Further, as the proximal end may be manipulated by healthcare workers during tube insertion and connection, in certain embodiments it may be advantageous for the proximal end portion 16 to be relatively rigid, with a hardness in the range of 84-90 Shore A. In a specific embodiment, at least a portion of the outer diameter of the proximal end portion 16 may be about 15-16 millimeters. Such a diameter may allow direct connection of the proximal end portion 16 to the ventilator tubing, which may eliminate a connection piece, providing cost and convenience advantages.

The endotracheal tube 10 may also include any suitable number of lumens (not shown) that may be appropriately sized and shaped for inflation, deflation, or suction. In one embodiment, a lumen may be operatively connected to the intermediate portion 14 to assist inflation or deflation. In another embodiment, a lumen may be disposed on the tube 10 and may terminate in notch or hole in the proximal portion 16 placed directly above the shoulder of the intermediate portion 14 that allows suction of any secretions that may build up on the top shoulder of the intermediate portion.

The intermediate portion 14 of the endotracheal tube 10 includes a structure capable of expanding in diameter. As depicted in FIG. 1, the intermediate portion 14 is in a partially expanded state. The intermediate portion 14 may contract such that its inner diameter is relatively smaller than the inner diameter of the proximal end portion 16 or the distal end portion 12. It should be understood that inner diameter of the endotracheal tube 10 may generally be measured from interior wall to interior wall of the tube, and the outer diameter may be measured from the exterior wall to exterior wall. Further, a maximum expandable outer diameter of the intermediate portion may be measured prior to insertion into a patient, as an intermediate portion 14 may assume a diameter larger than a tracheal diameter when fully expanded but not inserted into a patient. After insertion into a patient, the maximum outer diameter of the intermediate portion 14 may generally conform to the tracheal diameter, because the outer diameter can only expand as much as the trachea will allow. In certain embodiments, the intermediate portion 14 may have a range of maximum possible inner or outer diameters that may range from two times the size of an average trachea to half the size of the average trachea or smaller. Further, the portion 14 may taper or vary in diameter along its length. It should be understood that an average trachea size may be an adult male or female average size that is based on height and weight, or a child average size. For example, an adult trachea may range in size from 14 mm to 27 mm, with the average being around 20 mm. In one embodiment, the maximum expanded inner diameter of the intermediate portion 14 may be only slightly smaller than the outer diameter, and may range from 10 mm to slightly less than 60 mm. However, any suitable inner diameter/outer diameter combination is contemplated, and may depend on the size of the patient and the use of the device (e.g. veterinary use).

The intermediate portion 14 may also contract to have minimum inner and outer diameters that are suitably small to allow the intermediate portion 14 to be easily inserted into the trachea. In certain embodiments, the contracted inner or outer diameter may be 1-10 mm. However, any suitable contracted inner diameter/outer diameter combination is contemplated.

The intermediate portion 14 may be formed from materials having suitable mechanical properties (such as puncture resistance, pin hole resistance, tensile strength), chemical properties, and biocompatibility. In one embodiment, the walls of the intermediate portion 14 are made of polyurethane having suitable mechanical and chemical properties. An example of a suitable polyurethane is Dow Pellethane® 2363-80A or 80AE. In another embodiment, the walls of the intermediate portion 14 are made of a suitable PVC. Suitable materials may also include polyethylene teraphthalate (PET), low-density polyethylene (LDPE), polypropylene, silicone, neoprene, or polyisoprene.

In certain embodiments, the intermediate portion 14 may have relatively thinner tube walls than the proximal end portion 16 and the distal end portion 12. For example, an intermediate portion 14 may have tube walls that are sufficiently thin to fold in on themselves in order to conform to a patient tracheal diameter. The intermediate portion 14 tube walls may be between 5 microns 10 microns and 3 millimeters in thickness. In certain embodiments, the intermediate portion 14 walls are between 0.2 mils (where mils are thousandths of an inch) and 3 mils. Further, in certain embodiments, the intermediate portion 14 may be such that it may assume a slightly curved shape when expanded inside the trachea. A slightly curved design may reduce kinking in the endotracheal tube 10 that may result from outside forces acting on the device.

In certain embodiments, the proximal end portion 16, the distal end portion 12, and intermediate portion 14 may be formed from the same material in an extrusion manufacturing process. In such an embodiment, in order to obtain the varying wall thicknesses of the different sections of the endotracheal tube 10, a programmable parasin may be used to vary the wall thickness along the extruded portion. Further, after extrusion of a suitable length of tube containing all three portions, the intermediate portion 14 may be subjected to a blow-molding process in order to achieve decreased tube wall thickness and increased tube wall flexibility. For example, the endotracheal tube 10 may also be made by using preextruded tubing and applying heat and pressure appropriately within a molding cavity to achieve the desired shape (blow molding).

These endotracheal tubes 10 can also be formed by extrusion blow-molding, wherein an extruder fed polymer pellets melts the polymer and feeds the molten polymer through a die to form a tube shape. This still molten polymer is then captured in a mold and air pressure is applied to expand the tube out to the walls of the mold, thus achieving the desired shape. In the extrusion blow molding process, a core or mandrel of the extruder has apertures to admit a gas such as pressurized air or an inert gas like nitrogen, into the medical device. After a length of medical device has been extruded, a mold clamps the medical device around the mandrel. As gas is admitted to the intermediate portion 14 area through the mandrel, the intermediate portion 14 expands against the mold.

In the alternative, the intermediate portion 14 wall may be expanded in a second discrete expansion process following an extrusion or molding process, such as with a shuttle blow molding process. This process results in the area of the tube with larger diameters having thinner walls because the same amount of material is stretched over a larger area. The variable wall thickness, along the length of the endotracheal tube 10 may also be specified in the blow molding process by using a programmable parasin on the extruder. A programmable parasin allows the wall thickness being extruded to be controlled as a function of length. Therefore, the extruded section may have walls of varying thickness.

Figure 3:
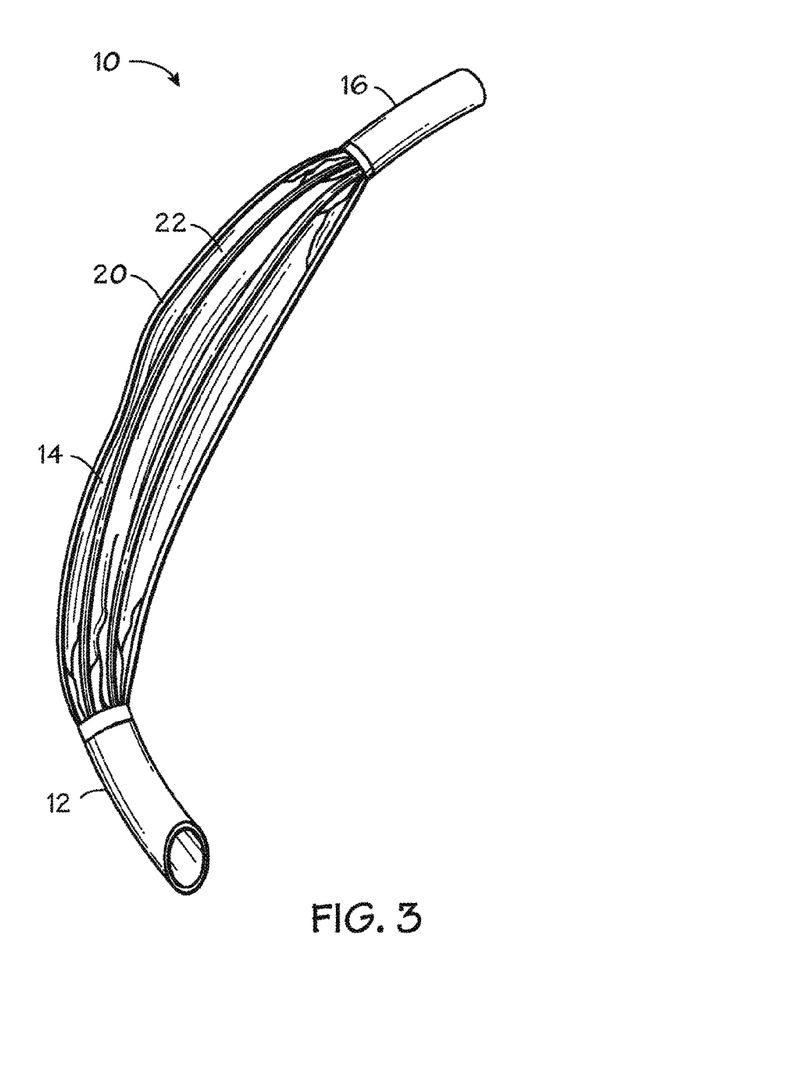
FIG. 3 illustrates an endotracheal tube with a ribbed expandable intermediate portion in accordance with aspects of the present invention

FIG. 3 depicts a specific embodiment in which the intermediate portion 14 of an endotracheal tube 10 may include expandable regions 22 separated by ribs 20. The ribs 20 are relatively rigid compared to the expandable regions 22. As depicted, the intermediate portion is in a partially expanded state. However, when fully collapsed, the ribs 20 may be touching or almost touching while the expandable regions 22 may fold in on themselves, allowing the intermediate portion 14 to substantially decrease its inner and outer diameters. Upon application of an expanding force or apparatus, such as those described herein, the flexible expandable regions 22 may unwrinkle and assume their full size, allowing the inner diameter of the intermediate portion 14 to increase. For example, the intermediate portion 14 may be expanded by positive pressure provided by a downstream medical device, such as a ventilator. In other embodiments, the intermediate portion 14 may be expanded by a removable stent-like apparatus that may be removed prior to removal of the endotraheceal tube 10.

The ribs 20 provide the advantage of added stability to the intermediate portion, which may ease insertion of the endotracheal tube 10 into the trachea. In specific embodiments, it is envisioned that the ribs 20 may be as hard as the proximal end 16 or distal end 12 (e.g. 84-90 Shore A or 70 shore A). Further, the ribs 20 may be extruded with the expandable regions 22 as part of a single mold by varying the thickness of the mold to accommodate the ribs 20.

Figure 4:
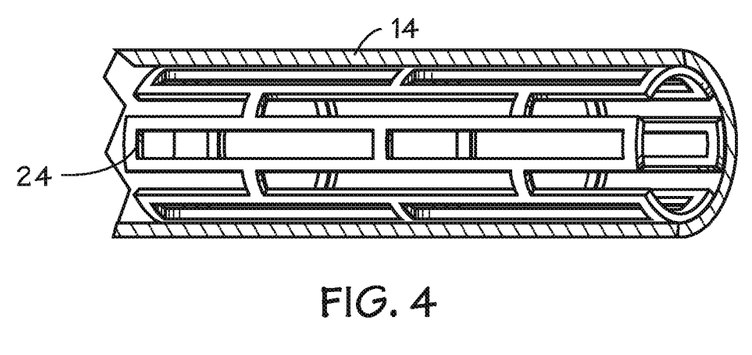
FIG. 4 illustrates a tracheal tube with an expandable backbone in its non-expanded state.
Figure 5:
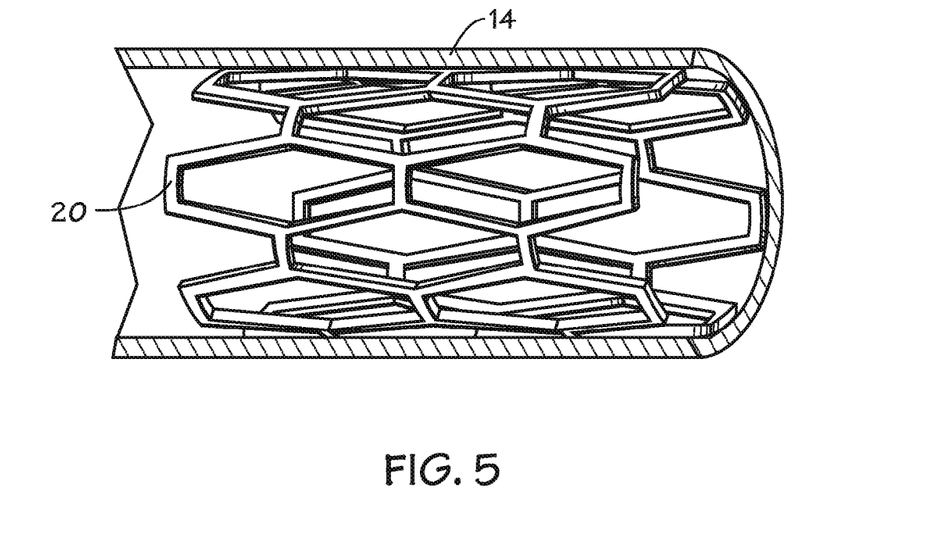
FIG. 5 illustrates the tracheal tube with an expandable backbone of FIG. 4 in its expanded state.

In an alternative embodiment depicted in FIGS. 4 and 5, the intermediate portion 14 may include an expandable backbone 24. The expandable backbone 24 may be formed from a mesh structure that may be made from any suitable material such as a metal or a polymer. Such an embodiment may provide the advantage of increased rigidity to the flexible intermediate portion 14 during intubation. In addition, the expandable backbone 24 may help maintain the shape of the intermediate portion 14 while the intermediate portion 14 is in its expanded state. In certain embodiments, the expandable backbone 24 may be located on the interior of the intermediate portion 14, or it may be embedded in the intermediate portion 14. In such an embodiment, the walls of the intermediate portion 14 may be sufficiently elastic to allow the expandable backbone 24 to expand fully.

An expandable backbone 24 is shown in its non-expanded state in FIG. 4 and its expanded state in FIG. 5. The cellular design of the expandable backbone 24 is meant to be illustrative, and it should be understood that other configurations and designs, such as coil, mesh or zigzag designs, may be appropriate. Any suitable expandable design may be used for the expandable backbone 24 of the present invention. In certain embodiments, the cells may be appropriately shaped as to maintain sufficient contact with the tracheal walls such that a seal may be sustained.

As mentioned above, the expandable backbone 24 should generally have sufficient elasticity, flexibility, and rigidity to be navigated through the larynx and trachea so that it does not abrade the patient's airway. Further, the expandable backbone 24 may be formed in a slightly curved configuration that may improve insertion into the trachea. Accordingly, stainless steel and other common alloys may be used for the expandable backbone 24. These materials are useful since their flexibility and high mechanical stability ensure they will be expandable and collapsible while at the same time capable of holding their form while in an expanded state to form a seal against the trachea. The material from which the expandable backbone 24 is formed may have sufficient flexibility to allow for flexing and movements of the trachea. However, one consideration is that the expandable backbone 24 not be so rigid as to be abrasive or to apply undue pressure against the tracheal walls. Additionally, the expandable backbone 24 may be formed from polymeric materials such as polyethylene terephthalate (PETP), polyurethane and various acrylate compositions.

In certain embodiments, the expandable backbone 24 may be formed from a shape memory material such as nitinol. In such embodiments, the expandable backbone 24 may be substantially stable in both the expanded conformation and the collapsed conformation. Mechanical force, such as force applied from an expanding apparatus, may be sufficient to trigger the change from the collapsed state to the expanded state. The expanded state may be also collapsed by the application of force along at least a portion of the intermediate portion 14. In other embodiments, the expandable backbone 24 may be mechanically "locked" into an expanded conformation range by mechanical features in the backbone design. For example, a diamond-shaped mesh design may include joints at its points that lock into one more possible expanded diameters.

Regardless of the materials used, the expandable backbone 24 may not only support the flexible intermediate portion 14 of the endotracheal tube 10 but may also be physically attached to the intermediate portion 14 by any suitable method, such as with adhesives, mechanical connections, or heat bonding. One advantage of having the expandable backbone 24 physically attached to the intermediate portion 14 is that it would prevent the two from axially sliding relative to each other. In addition, before extubation, both the expandable backbone 24 and the intermediate portion 14 may be collapsed from their expanded states. Having the two physically attached would assist during the collapsing process. However, due to the expandable nature of the intermediate portion 14, it may be useful to restrict physical attachment of the expandable backbone 24 and intermediate portion 14 to certain strategic locations, allowing the intermediate portion 14 more freedom of motion during expansion and collapse. As mentioned above, an important consideration is that the expandable backbone 24 and intermediate portion 14 may move in unison during the collapsing process prior to extubation.

Figure 6:
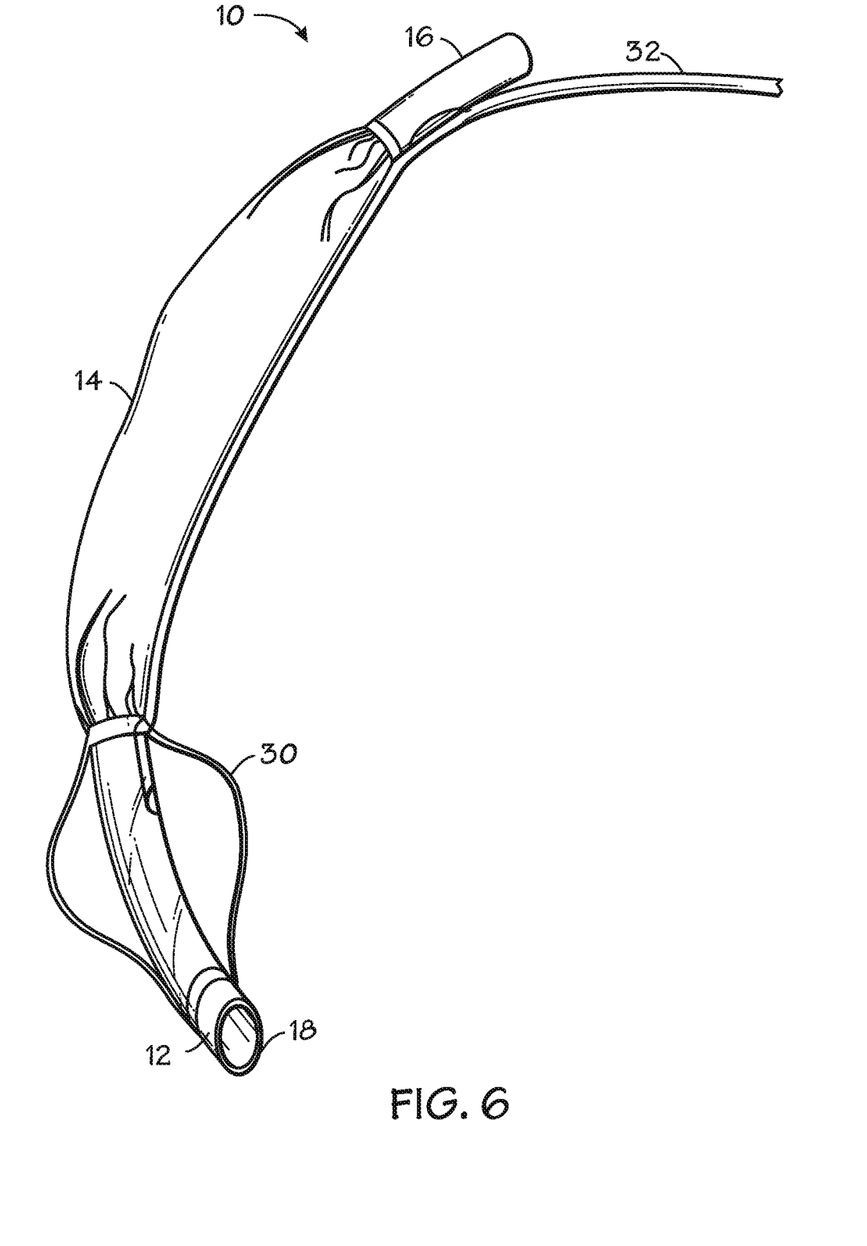
FIG. 6 illustrates an endotracheal tube with an expandable intermediate portion as well as an inflatable balloon cuff.

In certain embodiments, an inflatable balloon cuff 30 as depicted in FIG. 6 may be used in conjunction with the endotracheal tube 10. In this embodiment, the inflatable balloon cuff 30, instead of the intermediate portion 14, forms the seal against the trachea walls. Typically, the inflatable balloon cuff 30 is disposed, adhesively or otherwise, towards the distal end of the endotracheal tube 10 below the vocal cords. The inflatable balloon cuff 30 may be inflated and deflated via a lumen 32 in communication with the inflatable balloon cuff 30, typically through a hole or a notch in the endotracheal tube 10. Further, a lumen (not shown) may be disposed on the tube in order to suction off any secretions that may build up on the cuff 30.

The inflatable balloon cuff 30 may be formed from materials having suitable mechanical properties (such as puncture resistance, pin hole resistance, tensile strength), chemical properties (such as forming a suitable bond to the endotracheal tube 10), and biocompatibility. In one embodiment, the walls of the inflatable balloon cuff 30 are made of polyurethane having suitable mechanical and chemical properties. An example of a suitable polyurethane is Dow Pellethane® 2363-90A or 90AE. In another embodiment, the walls of the inflatable balloon cuff 30 are made of a suitable polyvinyl chloride (PVC). Suitable materials may also include polyethylene teraphthalate (PET), polyethylene (PE), polypropylene, silicone, neoprene, or polyisoprene.

Figure 7:
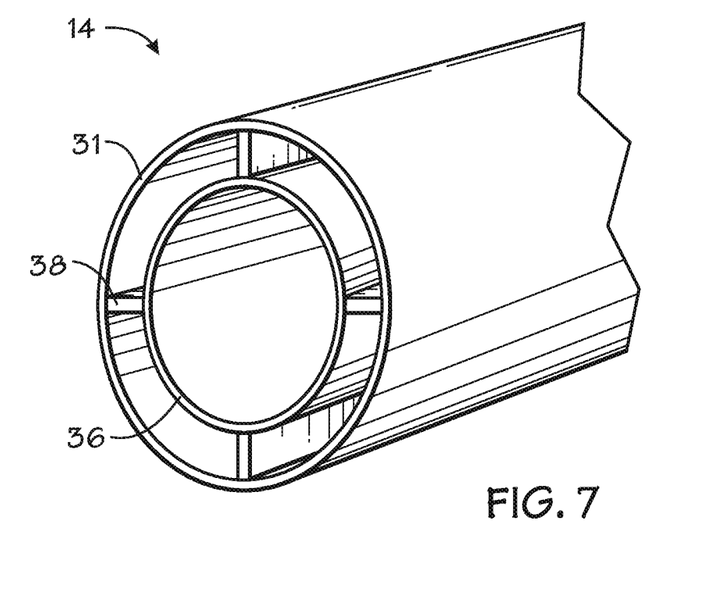
FIG. 7 illustrates an endotracheal tube with a concentric expandable intermediate portion in accordance with aspects of the present invention.
Figure 8:
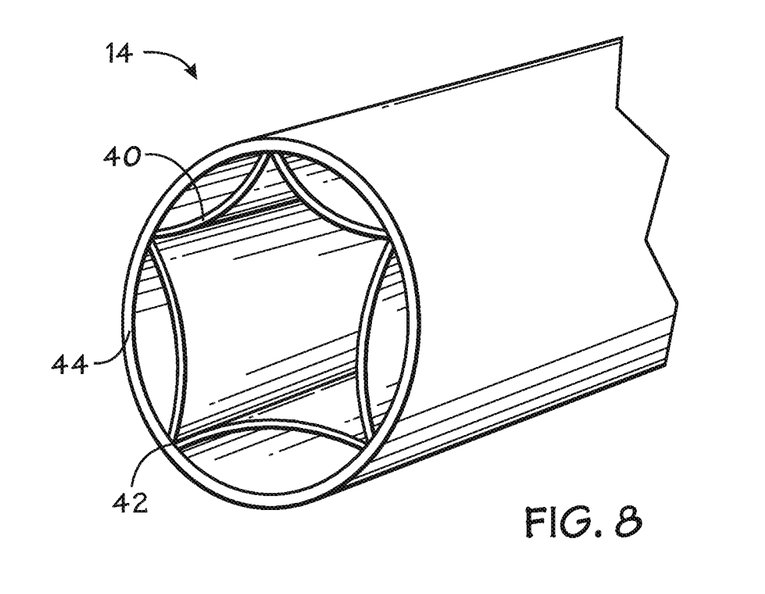
FIG. 8 illustrates an endotracheal tube with an alternative embodiment of a concentric expandable intermediate portion in accordance with aspects of the present invention.

The intermediate portion 14 may also include a double-layered structure in order to facilitate expansion and collapse. As shown in FIGS. 7 and 8, such a double-layered structure may include an inflatable gap between the two layers that may allow the outer diameter of the intermediate portion 14 to expand towards the tracheal walls while simultaneously increasing its inner diameter. FIG. 7 shows an exemplary intermediate portion 14 that includes a concentric outer layer 31 and inner layer 36 that are attached to one another by connecting members 38. It is envisioned that the gap between the inner layer 36 and the outer layer 31 may be filled with air or any suitable fluid via a lumen or other inflation device (not shown) in order to expand the inner diameter of the intermediate portion. The connecting members 38 may include holes to allow a single lumen to inflate the gap between the inner layer 36 and the outer layer 31. Alternatively, several lumens may be used such that each isolated gap may be filled with air. As the outer layer 31 expands towards the tracheal walls, inner layer 36 may be pulled along with it by the connecting members 38 in order to increase the inner diameter of the intermediate portion 14. The connecting members 38 may be polymeric, and they may be flexible or rigid. In an alternative embodiment, an exemplary double-layered intermediate portion is depicted in FIG. 8 which an inner layer 40 is attached to an outer layer 44 at several attachment points 42 along the intermediate portion. As the inner layer 40 is coupled to the outer layer 44, when the outer layer 44 expands towards the tracheal walls, the inner layer is pulled along, expanding the inner and outer diameters of the intermediate portion 14. The inner layer 40 and the outer layer 44 may be spot welded together at only a few attachment points 42 to leave a generally open space between them, such that the space between them may be inflated by a single inflation lumen.

Figure 9:
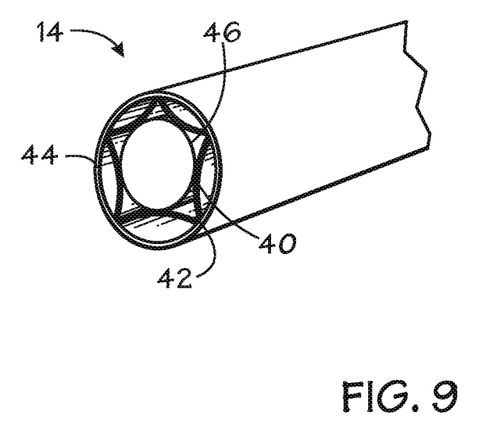
FIG. 9 illustrates a contracted tracheal tube with a concentric expandable intermediate portion that is contracted around a stylet in accordance with aspects of the present invention.
Figure 10:
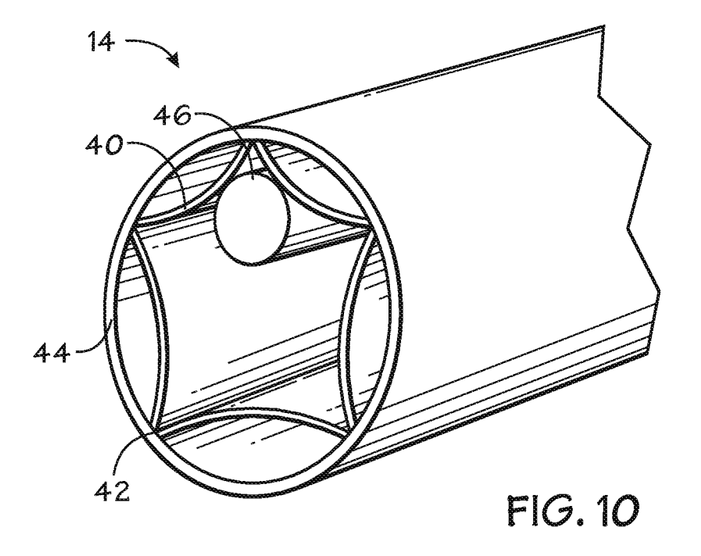
FIG. 10 illustrates an expanded tracheal tube with a concentric expandable intermediate portion and the sylet in accordance with aspects of the present invention.

The tracheal tube may also be inserted into the trachea with the aid of a stylet, in order to facilitate insertion, as well as expansion and collapse. As shown in FIGS. 9 and 10, a double-layered structure may be inserted in the collapsed state, depicted in FIG. 9, where the intermediate portion 14 is collapsed to closely conform to the diameter of a stylet 46. Both the inner layer 40 and the outer layer 38 may be generally draped, or furled, around the stylet 46. After insertion, the inner 40 and outer layer 44 may expand towards the tracheal walls, as shown in FIG. 10, and the inner layer 40 may pulled along with the outer layer 44, expanding the inner and outer diameters of the intermediate portion 14. After successful insertion and inflation, the stylet 46 may be removed, or, in an alternate embodiment, may remain substantially attached to the intermediate portion 14.

Figure 2:
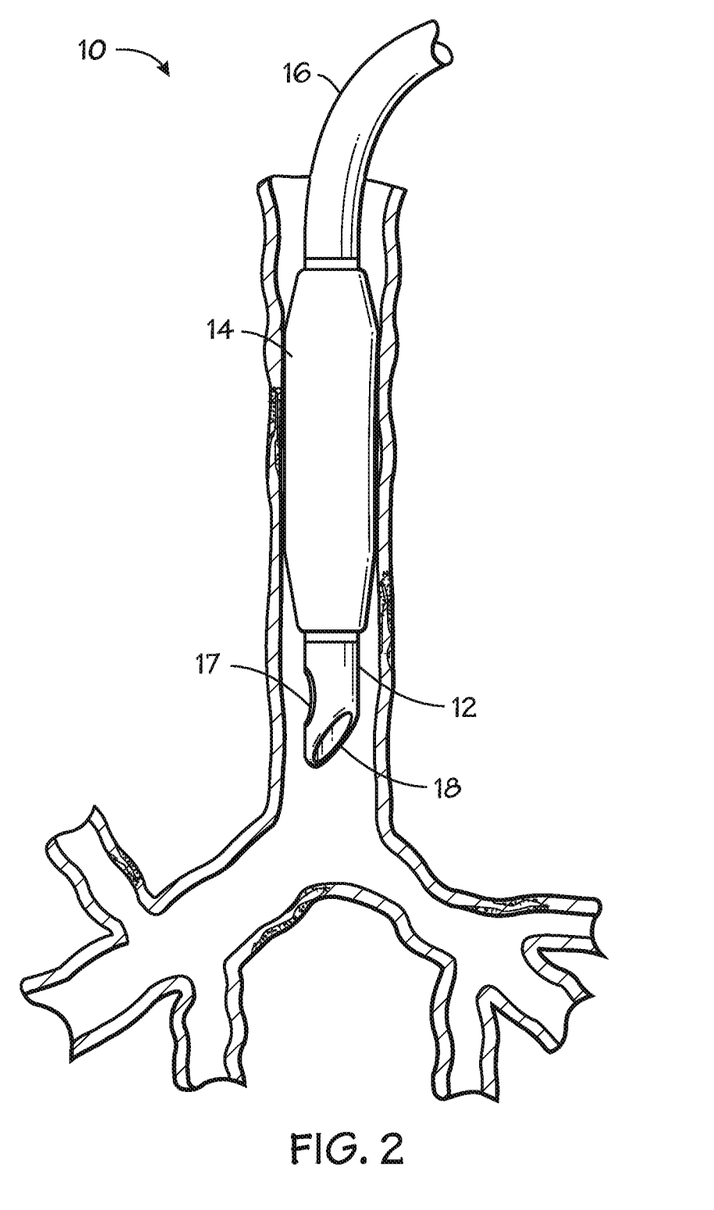
FIG. 2 illustrates an endotracheal tube with an expandable intermediate portion inserted into a patient's trachea.

Generally, after the endotracheal tube 10 is inserted into a patient's trachea, the diameter of the intermediate portion 14 may be expanded to conform to the tracheal walls, as depicted in FIG. 2. The intermediate portion 14 may inflated to form a seal against the tracheal walls and may prevent secretions or other detritus from passing through the trachea into the lungs. The intermediate portion may be inflated inside the patient's trachea such that its pressure against the tracheal walls is approximately 20-30 cm $H_2O$. The intermediate portion 14 may also include a safety mechanism or other feature designed to prevent the pressure from exceeding a predetermined pressure, such as 50 cm $H_2O$. For example, the intermediate portion 14 may include a pressure valve to allow rapid deflation of the intermediate portion 14. Alternatively, the intermediate portion 14 may include a pop-off section, which is designed to rip or tear at excessive pressures. Such a portion may be made from generally more fragile or thinner material than the rest of the intermediate portion 14.

Possible methods of expansion include mechanical, pneumatic, and/or thermal methods. In one embodiment, radial expansion of the intermediate portion 14 may be accomplished by a mechanical method. Under this method, a mechanical expanding apparatus may be inserted within the interior of the intermediate portion 14 before intubation. After intubation, this mechanical expanding apparatus may be used to radially expand the intermediate portion 14 until the intermediate portion 14 contacts the tracheal walls. After radial expansion of the intermediate portion 14, the mechanical expanding apparatus may be collapsed to its original configuration and removed from within the endotracheal tube 10. In certain embodiments, the intermediate portion 14 may be constructed from materials with shape memory, such as Nitinol, having a bi-stable configuration. In such embodiments, the expanded state of the intermediate portion 14 may have sufficient rigidity to maintain its general shape after the expanding apparatus has been removed. The mechanical expanding apparatus may also serve the secondary function of a stylet, which is typically used to guide an endotracheal tube into place within the trachea. Use of a stylet may also be advantageous in embodiments in which the intermediate portion 14 walls are soft and thin, as the stylet may provide additional rigidity or column strength to allow easier insertion of the endotracheal tube 10.

In another embodiment, radial expansion of the intermediate portion 14 may be accomplished by a pneumatic method. In this embodiment, an inflatable balloon may be inserted within the interior of the intermediate portion 14 before intubation. After intubation, the inflatable balloon may be inflated, radially expanding the intermediate portion 14 until it contacts the tracheal walls. After radial expansion of the intermediate portion 14, the inflatable balloon may be deflated and removed from within the endotracheal tube 10.

In an alternative pneumatic expansion, the distal end of the intermediate portion 14 may terminate with a pneumatic cap which is designed to yield at a certain pressure range. After intubation, radial expansion of the intermediate portion 14 may be accomplished by applying positive pressure within the endotracheal tube 10 from the proximal end of the endotracheal tube 10. The entire endotracheal tube 10 device may be designed such that the positive pressure would radially expand the intermediate portion 14 before the pneumatic cap yields to the pressure, at which point the airway of the endotracheal tube 10 may become opened. In another embodiment, the intermediate portion 14 may be inflated and deflated via a lumen in communication with the intermediate portion 14, typically through a hole or a notch in the endotracheal tube 10. In certain embodiments, the intermediate portion 14 may be operatively connected to a ventilator via the lumen to maintain a substantially constant pressure within the intermediate portion 14.

In yet another embodiment, radial expansion of the intermediate portion 14 may be accomplished by a thermal method. Under this method, the inherent physical properties of the material used for the intermediate portion 14 would allow the intermediate portion 14 to radially expand based merely on temperature differences. For instance, the material for the intermediate portion 14 may be selected such that its glass transition temperature would allow a collapsed state at room temperature and an expanded state at body temperature. In one embodiment, the intermediate portion 14 may include a shape-memory Nitinol, with a shape transition temperature close to body temperature. In such an embodiment, the shape-memory Nitinol expands when inserted into the body. Retraction may be accomplished by transferring cooled air through the intermediate portion 14.

Regardless of the method used to radially expand the intermediate portion 14, another method may be required to radially collapse the intermediate portion 14 before extubation. In one embodiment, radial collapsing of the intermediate portion 14 may be accomplished by a mechanical collapsing apparatus, converse to the mechanical expanding apparatus mentioned above. Before extubation, the mechanical collapsing apparatus may be inserted within the endotracheal tube 10 and physically attached to the intermediate portion 14. Any number of methods for physically attaching the mechanical collapsing apparatus may be used. However, one illustrative method is the use of a magnetized mechanical collapsing apparatus such that the expandable backbone 24, discussed below, is magnetically attracted to it. This method may be useful in embodiments in which stainless steel or other common alloy is used as the material for the expandable backbone 24. In another embodiment, radial collapsing of the intermediate portion 14 may be accomplished through suction.

Because the intermediate portion 14 may contact the tracheal walls during patient intubation, it is also envisioned that it may be advantageous for the intermediate portion 14 to have a gel coating on its outer diameter in order to place a soft, water-containing layer against the tracheal mucosa, instead of a harder plastic material. This gel coating may include biologically active agents, for example agents adapted to promote cell growth or cilia growth. In such an embodiment, therapeutic agents, such as growth factors, may be included on the tissue-contacting surface of the intermediate portion 14 as provided herein. Such agents may include therapeutically beneficial amounts of biologically active substances such as FGF (fibroblast growth factor), EGF (epidermal growth factor), PDGF (platelet-derived growth factor), IGF (insulin-like growth factor), TGF-β 1 through 3, cytokines, interferons, interleukins; hormones, insulin, growth hormone-releasing factor, calcitonin, and/or vitamins such as vitamin C, vitamin E, vitamin A or retinoic acid (e.g. trans-retinoic acid, 13-cis-retinoic acid, 9-cis-retinoic acid, other retinoids and mixtures thereof).

In a specific embodiment, the gel coating as provided herein may include a therapeutic quantity of a retinoic acid in order to promote cilia regeneration. A therapeutic agent such as a retinoic acid may be incorporated into a mucoadhesive layer disposed on the intermediate portion 14. In certain embodiments, the mucoadhesive layer includes at least 0.01% retinoic acid. It should be understood that in other embodiments, the retinoic acid or other therapeutic agent may also be incorporated on the surface of the intermediate portion 14 when a mucoadhesive layer is not present.

In other embodiments, it may be advantageous to provide that the gel coating include a therapeutic agent or a combination of therapeutic agents with a wide variety of biological activities. For example, the agent may include anti-inflammatory, anti-scarification, anticoagulant, antibiotic, antiallergic and antioxidant compounds. Examples of such anticoagulants include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax (Biogen, Inc., of Cambridge, Mass.). An example of an antiallergic agent is permirolast potassium. Other therapeutic substances or agents which may be appropriate include alpha-interferon, genetically engineered epithelial cells, rapamycin, dexamethasone, and functional analogs and structural derivatives thereof. The therapeutic agent may include peptides or proteins (such as enzymes, growth factors, hormones, and antibodies), small molecule compounds, nucleic acids, lipids, carbohydrates, steroids, glycoproteins, peptidomimetics, and/or oligodynamic metals.

The therapeutic agent may be applied to the surface of the intermediate portion 14 by techniques such as spraying, dipping, covalently bonding, extrusion blow-molding, or cross-linking the agent to the polymeric material of the intermediate portion 14. For example, the intermediate portion 14 may be dip-coated by dipping the intermediate portion 14 in a solution containing the compound for a sufficient period of time (such as, for example, five minutes) and then drying the coated intermediate portion 14, such as by means of air drying for a sufficient period of time. The agent may be chemically attached to the surface of the intermediate portion 14 through a two-step process surface activation through energy activation (e.g. plasma, pulsed plasma, flow discharge reactive chemistry (FDRC), corona discharge) or chemical activation, and subsequently chemically coupling the agent to the activated surface. Such coupling of the agent to the intermediate portion 14 may be accomplished through carbodiimide chemistry, reductive amination, malemide-thiol reactions, etc. Further, the therapeutic agent may be compounded with a polymer composition and extruded or molded onto the surface of the intermediate portion 14 as an outer layer, or it may be compounded into the intermediate portion 14 material itself.

In particular, the nature of the therapeutic agent may dictate its method of attachment to the intermediate portion 14. For example, retinoic acids tend to be relatively hydrophobic, and thus generally insoluble in water. In order to incorporate a retinoic acid onto a relatively hydrophilic surface, it may be advantageous to encapsulate the retinoic acid in amphipathic microspheres that shield the hydrophobicity of the retinoic acid from the hydrophilic polymer on the intermediate portion 14 walls. Such microspheres may enhance delivery of the retinoic acid to the mucosa. Proteins such as growth factors may also be encapsulated in microspheres to be applied to the surface of the intermediate portion 14. Nanoparticles may also be used to encapsulate or assist in attachment of therapeutic agents to the intermediate portion 14. Fullerenes, micelles or liposheres can all be functionalized to attach to specific surfaces and provide controlled-release of hydrophilic or hydrophobic molecules. Alternatively, dendromers can be assembled to contain specific binding sites or adhesion properties and allow for a high concentration of surface groups which may include one or more therapeutic agents.

The therapeutically beneficial agent may be adapted to be released from the intermediate portion 14 over time. For example, the therapeutic agents may be incorporated into a mucoadhesive layer that is adapted to degrade over time, which may allow release of the therapeutic agent. In other embodiments, a therapeutic agent such as an antimicrobial agent may be adapted to be released over time via a water-soluble glass. In such an embodiment, the intermediate portion 14 may include a metal with antimicrobial properties such as silver in a phosphorus-based glass material that dissolves in water at a rate that may be a function of its particular formulation. In one embodiment, a silver calcium phosphorus-based glass may be part of a polymer layer that is made up of about 5-10% by weight, e.g. about 7.5% silver calcium phosphorus-based glass by weight. Such a phosphorus-based glass is available from Giltech Limited, 12 North Harbour Industrial Estate, Ayr, Scotland, Great Britain KA8 8BN.

The endotracheal tube 10 of the present invention may be incorporated into systems that facilitate positive pressure ventilation of a patient, such as a ventilator. These systems may include connective tubing, a gas source, a monitor, and/or a controller. The controller may be a digital controller, a computer, an electromechanical programmable controller, or any other control system. In certain embodiments, the controller may vary the amount of pressure applied to an intermediate portion 14 in order to vary the inner diameter of the endotracheal tube 10. The variation may occur breath-to-breath in order to move the endotracheal tube 10 away from the patient's tracheal walls and reduce any discomfort associated with constant pressure of the intermediate portion 14 against the tracheal walls. For example, as the work of breathing by the patient is experienced during exhalation, it would be advantageous to have a larger diameter intermediate portion 14 to decrease the work of exhalation for the patient. However, as inspiration is facilitated by the pressure of the ventilator, the patient is generally passive during this step. Thus, decreasing the diameter of the endotracheal tube 10 may not substantially affect the patient's work of breathing. Therefore, the controller on the ventilator may regularly decrease the pressure associated with the intermediate portion 14 inflation during inspiration. For example, if the intermediate portion 14 is designed to contact the tracheal walls at pressures of 20-30 cm $H_2O$, a controller may decrease the intratube pressure to 10-15 cm $H_2O$. In such an embodiment, it may be advantageous to provide a cuffed endotracheal tube 10 in order to maintain positive pressure during such intervals in which intermediate portion 14 of the endotracheal tube is not sealed against the tracheal walls.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A tracheal tube comprising:
a tube defining a passageway for transferring respiratory gas to a patient's lungs, the tube comprising:
a distal end portion;
a proximal end portion; and
an intermediate portion co-axially coupled to the distal end portion and to the proximal end portion to form a conduit for transfer of the respiratory gas into a patient's trachea, wherein the intermediate portion comprises thin wall sections between longitudinal ribs coupling the proximal end portion to the distal end portion, wherein the thin wall sections are capable of folding in on themselves, and wherein the longitudinal ribs are more rigid than the thin wall sections, and wherein the thin wall sections and the longitudinal ribs form a portion of the conduit for transfer of the respiratory gas and are configured to directly contact the respiratory gas, wherein there is no structure on an interior side of the thin wall sections and longitudinal ribs.

2. The tracheal tube, as set forth in claim 1, wherein the ribs are adjacent to one other when the tracheal tube is in a collapsed state.

3. The tracheal tube, as set forth in claim 1, wherein the ribs are configured to move away from each other when the intermediate portion expands.

4. The tracheal tube, as set forth in claim 1, wherein the intermediate portion is configured to expand to a diameter at least equal to the diameter of a patient's trachea.

5. The tracheal tube, as set forth in claim 3, wherein a medical device is configured to apply positive pressure to the intermediate portion to expand the intermediate portion.

6. The tracheal tube, as set forth in claim 5, wherein the medical device comprises a ventilator.

7. The tracheal tube, as set forth in claim 1, wherein the tracheal tube does not comprise a balloon cuff coupled to an exterior of the tracheal tube.

* * * * *